United States Patent [19]
Ishiguro et al.

[11] Patent Number: 5,148,231
[45] Date of Patent: Sep. 15, 1992

[54] APPARATUS FOR MEASURING A REFRACTING POWER OF AN OPTICAL SYSTEM

[75] Inventors: Shinji Ishiguro; Toshiharu Morino, both of Nagoya, Japan

[73] Assignee: Tomey Corp., Nagoya, Japan

[21] Appl. No.: 721,292

[22] Filed: Jun. 26, 1991

[30] Foreign Application Priority Data
Jun. 26, 1990 [JP] Japan .................. 2-167315

[51] Int. Cl.⁵ .................. G01B 9/00; A61B 3/10
[52] U.S. Cl. .................. 356/126; 351/211
[58] Field of Search ........... 356/124, 125, 126, 127; 351/205, 211, 212, 214, 221

[56] References Cited
FOREIGN PATENT DOCUMENTS

| | | |
|---|---|---|
| 55-160538 | 12/1980 | Japan . |
| 57-165735 | 10/1982 | Japan . |
| 61-30570 | 7/1986 | Japan . |
| 61-280543 | 12/1986 | Japan . |
| 63-46130 | 2/1988 | Japan . |

*Primary Examiner*—F. L. Evans
*Attorney, Agent, or Firm*—Oblon, Spivak, McClelland, Maier & Neustadt

[57] ABSTRACT

An apparatus for measuring a refracting power of an optical system which comprises: a beam projecting optical system which projects a predetermined moving luminous flux to an optical system to be inspected; a beam condensing optical system in which a photoelectric conversion element receives a luminous flux transmitted through the optical system to be inspected; and a processing system which obtains the refracting power of the optical system to be inspected, based on an output from the beam condensing optical system; wherein a rotating plate having at least one tooth of a converging shape, which is protruded outwardly from a center of the rotating plate, is disposed in a beam path of the beam projecting system; and a luminous flux, both edges, in a moving direction thereof, of which are inclined to the moving direction with angles being different with each other and correspond to both sides of the tooth, irradiates the optical system to be inspected, by intermittently blocking the beam path by the tooth.

3 Claims, 7 Drawing Sheets

APPARATUS FOR MEASURING A REFRACTING POWER OF AN OPTICAL SYSTEM

This invention relates to an apparatus for measuring a refracting power of an optical system, and more particularly to an apparatus for measuring a refracting power of an optical system which can suitably be used as an objective refracting power measuring device of an eye and the like.

Formerly, a device is known, as a kind of device which measures a refracting power in various optical systems such as eyes of animals, or lenses for optical instruments. The refractive power is calculated in such optical system to be inspected, by moving a predetermined luminous flux and projecting the flux on the optical system to be inspected, and by detecting a transmitted beam through the optical system to be inspected, based on a moving direction, a velocity, or a twist of the transmitted beam. For instance, one is an autorefractometer having a basic principle of retinoscopy, in which a refracting power (cylindrical axis angle: $\theta$, spherical refracting power: S, cylindrical refracting power: C) in a human eye is objectively measured.

As is publicly known, at least two kinds of beams which differ from each other in their angles of inclination to, the moving direction, are necessary to be projected to an optical system to be inspected, in such refractometer, to obtain the refracting power of the optical system to be inspected from the moving direction, the velocity, and the twist, of the luminous flux being transmitted through the optical system to be inspected. For such purpose, conventionally, as disclosed in Japanese Unexamined Patent Publication Nos. 160538/1980 or 165735/1982, devices are utilized in which slit-like luminous fluxes of which angles of inclination are different from each other with respect to the moving direction, by rotating the whole device, or by utilizing a rotating prism. However, in such devices, there is a problem in which the sizes of the devices are magnified or the beam quantity is attenuated by the prism.

To cope with this problem, refracting power measuring devices are proposed, in which more than two slit-like luminous fluxes, the angles of inclination of which differ from each other with respect to the moving direction, are projected to the optical system to be inspected, by disposing a cylindrical light blocking body which is rotatable around its axis, in the beam path of the luminous flux, and by forming a plurality of straight slits having more than two different angles of inclination with respect to the rotation direction, on the light blocking body, as shown in Japanese Unexamined Patent Publication No. 280543/1986.

However, in such device, the formation of the light blocking body composed of a thin cylindrical body is difficult. Furthermore the light blocking body is easily deformable, and easily causes a center oscillation in the rotation by a motor. Therefore the light blocking body has a disadvantage in which a setting or an adjustment for preventing the center oscillation, is difficult, which may not maintain a sufficient measurement accuracy.

Therefore, the applicants, formerly, in Japanese Unexamined Patent Publication No. 46130/1988, proposed a refracting power measurement device in which a planar rotating plate is utilized, as a light blocking body which is disposed on the beam path of the luminous flux projected on the optical system to be inspected. A plurality of straight slits that are extended towards a radius direction with more than two different angles of inclination with respect to the radius direction, on that rotating plate. In such device, since a planar plate is utilized as a light blocking body, the forming thereof is easy, and the deformation and the center oscillation in the rotation etc. can favorably be prevented.

However, even in the device in which such planar rotating plate is utilized, since a plurality of slit-like luminous fluxes having different angles of inclination, as luminous fluxes which are projected to the optical system to be inspected, are utilized in order to obtain such luminous fluxes, it is necessary to form a plurality of straight slits having different angles of inclination with respect to the radius direction. The making thereof is quite difficult.

Furthermore, in such planar rotating plate, the slits are formed in straight shape inclined to the radius direction by a predetermined angle, a substantial angle of inclination, or an intersection angle to a line of radius direction of the rotating plate is different with a distance in the radius direction from a central axis of rotation. Therefore, when the blocking position of the beam path on the rotating plate, is changed in radius direction, the angle of inclination of the luminous flux which is obtained by the slit, is also changed, which may lower the measurement accuracy.

It is an object of the present invention to provide an apparatus for measuring a refraction capacity of an optical system capable of favorably obtaining a luminous flux which is projected to an optical system to be inspected, by having a new rotating plate, and being suitably applied to an eye refracting power measuring device, or a lens meter, or a measuring device for radius of curvature etc.

It is another object of the present invention to provide an apparatus for measuring a refracting power of an optical system having a rotating plate capable of effectively preventing a change of an inclination angle of a luminous flux projected on an optical system to be inspected, even when a blocking position of the beam path is radially changed on the rotating plate.

According to an aspect of the present invention, there is provided an apparatus for measuring a refracting power of an optical system which comprises:

a beam projecting optical system which projects a predetermined moving luminous flux to an optical system to be inspected;

a beam condensing optical system in which a photoelectric conversion element receives a luminous flux transmitted through the optical system to be inspected; and a processing system which obtains the refracting power of the optical system to be inspected, based on an output from the beam condensing optical system;

wherein a rotating plate having at least one tooth of a converging shape, which is protruded outwardly from a center of the rotating plate, is disposed in a beam path of the beam projecting system; and a luminous flux, both edges, in a moving direction thereof, of which are inclined to the moving direction with angles being different with each other and correspond to both sides of the tooth, irradiates the optical system to be inspected, by intermittently blocking the beam path by the tooth.

According to another aspect of the present invention, the both sides of the tooth of the rotating plate are formed in curves, which intersect with a circle being concentric with respect to a rotation center of the rotating plate by about constant intersecting angles, in a predetermined range of a radius of the circle.

Furthermore, a protective ring is favorably formed, which is disposed at a rotational periphery of the rotating plate of the refracting power measuring device according to the present invention, and which is integrally connected to a top portion of the tooth.

A more complete appreciation of the invention and many of the attendant advantages thereof will be readily obtained as the same becomes better understood by reference to the following detailed description when considered in connection with the accompanying drawings, wherein.

Figure 1:
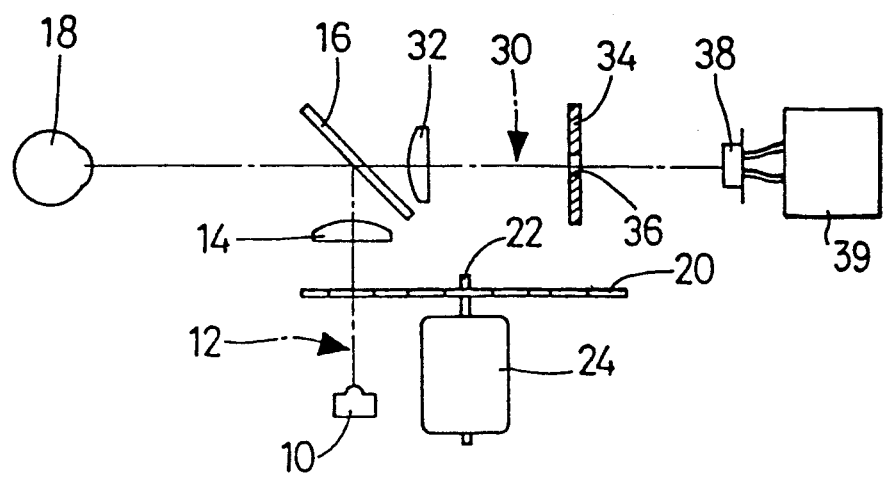
FIG. 1 is a basic construction diagram showing an outline of an embodiment of an eye refracting power measurement device according to the present invention.

Detailed explanation will be given to an embodiment of an eye refracting power measuring device according to the present invention, referring to the drawings.

First of all, FIG. 1 is a construction diagram of an embodiment of an eye refracting power measuring device according to the present invention. In FIG. 1, a numeral 10 designates a beam source. A beam from the beam source 10 is transmitted through the projecting lens 14, reflected by the half mirror 16, and projected to a pupil of the eye to be inspected 18, along the beam projecting path 12. Furthermore the projected beam is reflected by an eyeground of the eye to be inspected 18. The reflection beam penetrates through the half mirror 16, the condensing lens 32, and the stop 34, and irradiates the beam receiving part 38 along the beam condensing path 30. The reflection beam is detected by the beam receiving part 38 as an electric signal. The electric signal obtained by the beam receiving part 38, is inputted to a processing system 39. A refracting power of the eye to be inspected 18 is obtained by treating the electric signal for calculation by the processing system.

More particularly, the beam source 10 is composed of an infrared emission diode or the like. Furthermore, the beam from the beam source 10, is converted to an approximately parallel beam, by the projecting lens 14, and projected to the eye to be inspected 18 on the beam projecting path 12.

Figure 2:
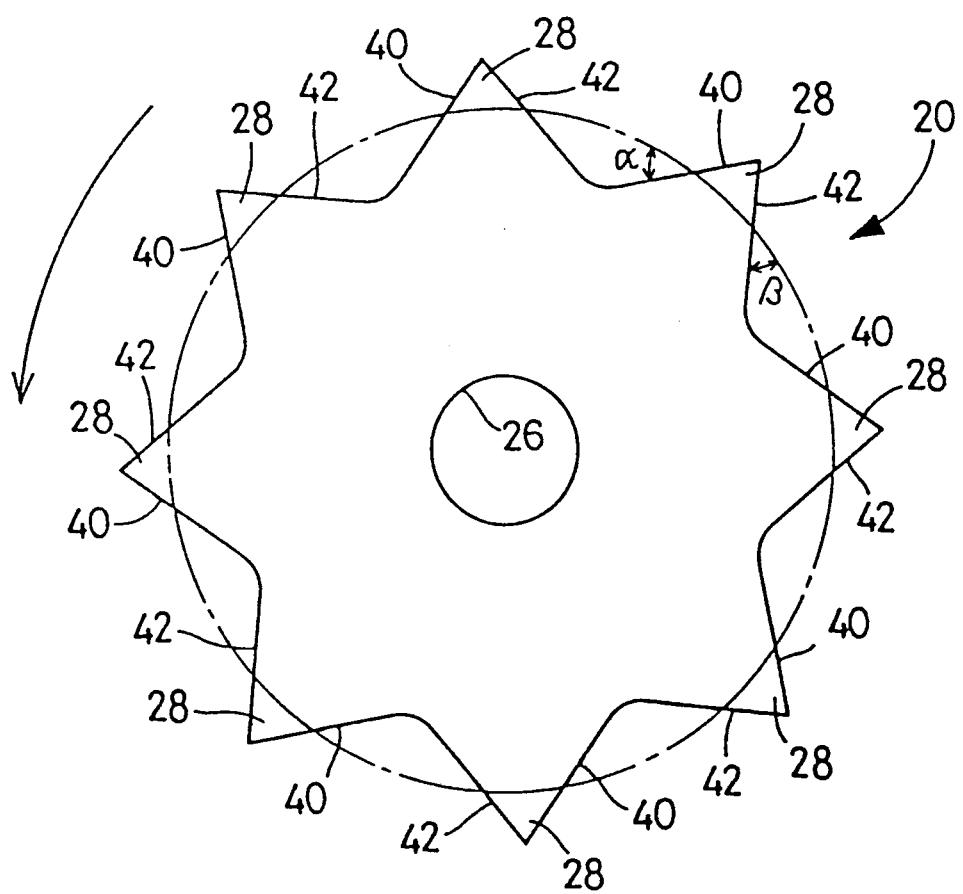
FIG. 2 is a front view showing a plate utilized in the eye refracting power measuring device.

On the beam projecting path 12, the approximately disc-like plate 20 is installed between the beam source 10 and the projecting lens 14. The plate 20 is rotated around the center by the motor 24 having the rotating shaft 22, approximately parallel with the beam axis of the projecting lens 14. This plate 20, as shown in FIG. 2, has the installing hole 26 for the rotating shaft 22 of the motor 24. On the other hand, the plate 20 is equipped with a plurality (8 in this embodiment) of the converging teeth 28 protruded toward the outward radius direction from the center, continuously allocated in the circumferential direction, at the outer periphery of the plate 20. Therefore in this embodiment, the outer periphery of the plate 20 is shaped in a sawtooth shape by the teeth 28.

The plate 20 is disposed to the projecting beam path 12 at a predetermined interval, so that the plate 20 blocks the beam projecting path 12, at the middle part of the teeth 28 in the protruding direction. By this arrangement, when the plate 20 is rotated, the projecting beam path 12 can intermittently be blocked by the teeth 28.

In the teeth 28 of the plate 20, both of the front side 40 disposed at the front side in the rotating direction of the plate 20, and the rear side 42 disposed at the rear side in the rotating direction of the plate 20, are made straight. The shapes of the respective teeth 28 are determined, as the intersection angle $\alpha$ remains the same for the respective teeth 28, which is an intersection angle of the front side 40 and the tangent line in circumferential direction at the intersection of the front side 40 and any circle centered on the rotation center of the plate 20. Furthermore, the intersection angle $\beta$ remains the same for respective teeth 28 which is an intersection angle of the rear side 42 and the tangential line in circumferential direction on the intersection of the rear side 42 and any circle centered on a rotation center of the plate 20. Particularly, in this embodiment, the intersection angles of the front side 40 and the rear side 42, with the tangent lines in circumferential direction, at the intersections of a circle which is a locus of a center of the beam projecting path 12 on the plate 20, refer each other with a relative angle difference of 90°. For instance, $\alpha$ and $\beta$ are set as $\alpha=45°$ and $\beta=45°$.

Accordingly, the beam from the beam source 10 to the projecting lens 14, is intermittently blocked by the teeth 28 of the plate 20 by the rotation of the plate 20 which is disposed on the beam projecting path 12, by which the luminous flux is moved in one direction. The luminous flux moves (scans) in a pupil of the eye to be inspected 18. The section of the luminous flux has a shape which corresponds to spaces among the teeth 28 juxtaposed on the plate 20. The both edges, in the moving direction, are inclined to the moving direction with angles different with each other, namely, with predetermined angles corresponding to the angles of inclination ($\beta$ and $\alpha$) of the rear side 42 and the front side 40 of the plate 20. In particular, in this embodiment, as apparent from the above explanation, the both side edges in the moving direction, of the luminous flux, have an inclination angle difference of 90° from each other.

Furthermore, as apparent in the above explanation, in this embodiment, a beam projecting optical system is so composed, as moving luminous fluxes are projected to the eye to be inspected 18, by the beam source 10, the projecting lens 14, the half mirror 16, and the plate 20.

In the luminous flux projected to the pupil of the eye to be inspected 18, a beam reflected by the eyeground, and transmitted through the half mirror 16, is collected by the condensing lens 32 disposed on the condensing beam path 30, and is irradiated to the beam receiving part 38 through the circular opening 36 of the stop 34 disposed on the rear side of the condensing lens 32. The beam receiving plane of the beam receiving part 38 is almost conjugated with a cornea of the eye to be inspected 18 by the condensing lens 32.

Figure 3:
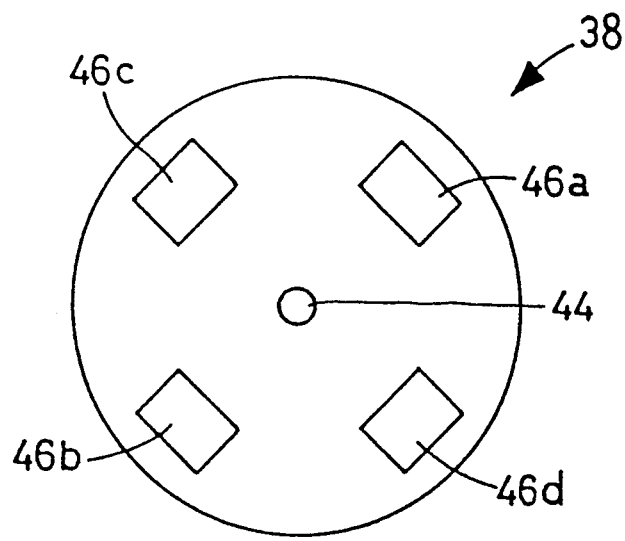
FIG. 3 is a front view showing a beam receiving part utilized in the eye refracting power measuring device.

In this embodiment, in the beam receiving part 38, as shown in FIG. 3, the photoelectric conversion element 44 for alignment, allocated at the center of the beam axis and four photoelectric conversion elements 46a, 46b, 46c, and 46d, which are located independently at the outside of the beam axis, are provided on the beam receiving plane. As is publicly known, by the existence of an output of a corneal reflection beam at the photoelectric conversion element 44, the deviation between the measuring device and the eye to be inspected 18 is detectable.

On the other hand, the four photoelectric conversion element 46 allocated on the beam receiving plane of the beam receiving part 38, are respectively disposed about a same circle which is centered on the beam axis. Among these photoelectric conversion elements, the photoelectric conversion elements 46a and 46b are symmetrically disposed with respect to the beam axis, whereas the other photoelectric conversion elements 46c and 46d are symmetrically disposed with respect to the beam axis. As explained in FIGS. 4 and 5, the photoelectric conversion elements 46a and 46b are disposed on the beam receiving plane, with an inclination angle corresponding to an inclination angle of the front edge in the rotation direction of the luminous flux projected to the eye to be inspected 18. The other couple of the photoelectric conversion elements 46c and 46d, are disposed on the beam receiving plane, with an inclination angle corresponding to an inclination angle of the rear edge in the rotation direction of the luminous flux projected to the eye to be inspected 18. Accordingly, in this embodiment, a couple of photoelectric conversion elements 46a and 46b, and the other couple of the photoelectric conversion elements 46c and 46d, are respectively disposed, on straight lines having an inclination angle difference of 90° at the intersection on the beam axis.

As apparently shown in the above, in this embodiment, a beam condensing optical system is composed, in which the photoelectric conversion elements receive the reflection beam from the eyeground of the eye to be inspected, of the luminous flux projected by the beam projecting system, of the condensing lens 32, the stop 34, and the beam receiving part 38.

Furthermore, the eye refracting power measuring device in this embodiment, has a processing system 39 in which an electric signal is inputted which is outputted from the beam receiving part 38 which constitutes the beam condensing optical system, when the moving luminous flux is projected to the eye to be inspected 18, under the operation of the beam projecting optical system. In this processing system, a refracting power of the eye to be inspected 18 is calculated based on the phase difference of the electric signals of ON-OFF or OFF-ON, which are outputted by the respective photoelectric conversion elements 46a to 46d in the beam receiving part 38.

Figure 4:
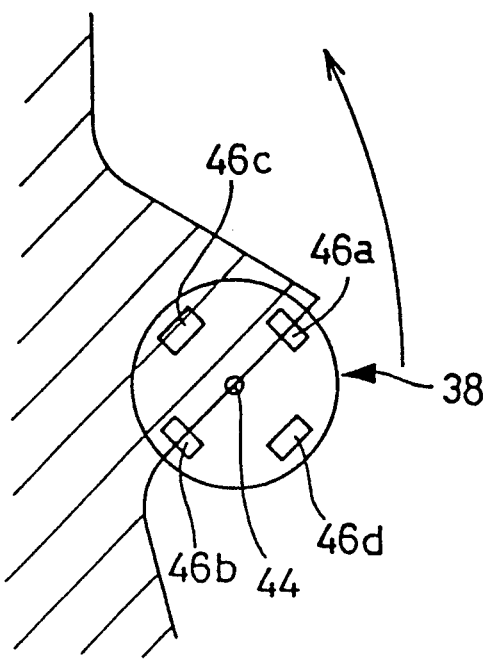
FIG. 4 is an explanatory diagram showing a moving mode of a reflection beam on a beam receiving plane of the beam receiving part, when an eye to be inspected is scanned by a front edge of a luminous flux, in the eye refracting power measuring device shown in FIG. 1.
Figure 5:
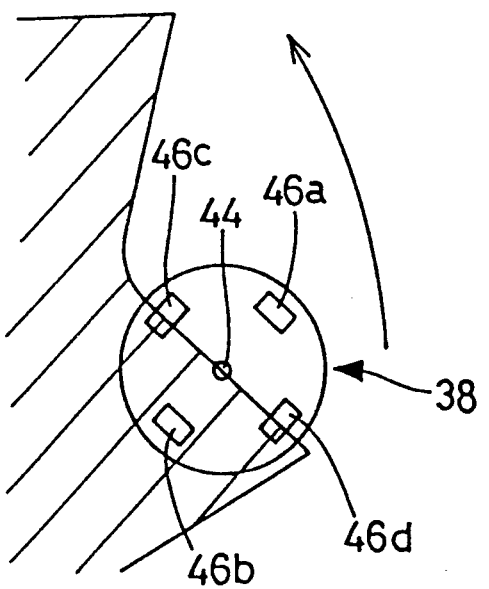
FIG. 5 is an explanatory diagram explaining the moving mode of the reflection beam on the beam receiving plane of the beam receiving part when an eye to be inspected is scanned by a rear edge of the luminous flux.

To be more concrete, first of all, when there is no astigmatism in the eye to be inspected 18, the luminous flux projected to the eye to be inspected 18, does not receive a twist around the beam axis which is caused by the eye to be inspected. Accordingly, when the front edge in the moving direction in the above luminous flux, scans the eye to be inspected, as shown in FIG. 4, electric signals with no phase difference are outputted, which are simultaneously made ON from OFF, from the couple of the photoelectric conversion elements 46a and 46b on the beam receiving part 38 which receives the reflection beam of the luminous flux. On the other hand, electric signals are outputted, which are made ON from OFF, respectively, with a phase lag corresponding to the moving speed of the reflection beam on the beam receiving part 38, from the other couple of photoelectric conversion elements 46c and 46d. After that, when the luminous flux moves on the eye to be inspected 18, and the rear edge in the moving direction of the luminous flux, scans the eye to be inspected 18, as shown in FIG. 5, the same electric signals with no phase difference are outputted, which are simultaneously made OFF from ON, from the photoelectric conversion elements 46c and 46d. On the other hand, the electric signals are outputted respectively, which are made OFF from ON, from the other couple of photoelectric conversion elements 46a and 46b, with a phase lag corresponding to the speed of the reflection beam on the beam receiving part 38.

Accordingly, the eye to be inspected 18 is judged to have no astigmatism, when neither of the output signals of the photoelectric conversion elements 46a and 46b in the case where the front edge part in the moving direction of the luminous flux, scans the eye to be inspected 18, and the output signals of the photoelectric conversion elements 46c and 46d, in the case where the rear edge in the moving direction of the luminous flux, scans the eye to be inspected 18, have no phase difference, and when the phase difference between the output signals of the photoelectric conversion elements 46c and 46d in the case where the front edge part in the moving direction of the luminous flux, scans the eye to be inspected 18, and the phase difference between the output signals of the photoelectric conversion elements 46a and 46b, in the case where the rear edge in the moving direction of the luminous flux, scans the eye to be inspected 18, are the same. Furthermore, in that occasion, the moving direction and the velocity of the luminous flux on the beam receiving plane of the beam receiving part 38, namely, the moving direction and the velocity of the luminous flux at the eyeground of the eye to be inspected 18, can be obtained, from the phase difference between the output signals of the photoelectric conversion elements 46c and 46d in case that the front edge in the moving direction of the luminous flux, scans the eye to be inspected 18, or by the phase difference in the output signals of the photoelectric conversion elements 46a and 46b in the case where the rear edge in the moving direction of the luminous flux, scans the eye to be inspected 18. Therefore, as shown in the above Japanese Unexamined Patent Publication No. 160538/1980, the refracting power (spherical refracting power: S) in the eye to be inspected 18, can be calculated in the above processing system, based on the relationship among the moving direction and the velocity of the luminous flux at the eyeground of the eye to be inspected 18, and the moving direction and the velocity (rotation speed of the plate 20) of the luminous flux projected to the eye to be inspected 18.

Next, when there is an astigmatism in the eye to be inspected 18, as is publicly known, the luminous flux projected on the eye to be inspected 18, is twisted around the beam axis by the angle ($\theta$) which corresponds to the direction of the main longitudinal line of the astigmatism with respect to the moving direction of the luminous flux, by the eye to be inspected 18.

Accordingly, by the twist around the beam axis, a phase difference is generated not only between the output signals of a couple of the photoelectric conversion elements 46c and 46d on the beam receiving part 38 but also between the output signals of the other pair of the photoelectric conversion elements 46a and 46b, in the case where the front edge in the moving direction of the luminous flux, moves on the eye to be inspected 18. Furthermore, a phase difference is generated not only between the output signals of a couple of photoelectric conversion elements 46a and 46b on the beam receiving part 38, but also between the other couple of photoelectric conversion elements 46c and 46d, in the case where the rear edge in the moving direction of the luminous flux moves on the eye to be inspected 18. These output signals having such phase differences, have an information concerning the spherical refracting power (S) in the eye to be inspected 18, as well as of cylindrical axis angle ($\theta$) and cylindrical refracting power (C). Furthermore, when one of the direction of the main longitudinal lines of the astigmatism agrees with the direction of a line connecting the couple of the photoelectric conversion elements 46a and 46b or 46c and 46d, no phase differences are generated between the output signals of the photoelectric conversion elements 46a and 46b in case that the front edge in the moving direction of the luminous flux, moves on the eye to be inspected 18, and between the output signals of the photoelectric conversion elements 46c and 46d, in case that the rear edge in the moving direction of the luminous flux, moves on the eye to be inspected 18. In such occasion, by the twist of the projected luminous flux around the beam axis, the phase difference, between output signals of the photoelectric conversion elements 46c and 46d in case that the front edge in the moving direction of the luminous flux, moves on the eye to be inspected 18, and the phase difference between the output signals of the photoelectric conversion elements 46a and 46b in the case where the rear edge in the moving direction of the luminous flux, moves on the eye to be inspected 18, are not the same, which enables detection of the astigmatism. These output signals having such phase differences, have an information concerning the refracting power of the eye to be inspected 18.

A value is determined to be $D_1$ which is obtained as a spherical refracting power based on an equation in case of no above mentioned astigmatism, from a phase difference of the electric signal from OFF to ON, which is outputted from the couple of the photoelectric conversion elements 46a and 46b on the beam receiving part 38, in case that the front edge in the moving direction of the luminous flux, scans the eye to be inspected 18, and a value is determined to be $D_2$ which is obtained as a spherical refracting power based on the equation in case of no astigmatism, from the phase difference of the electric signals from ON to OFF, which is outputted from the other couple of the photoelectric conversion elements 46c and 46d in case that the front edge in the moving direction of the luminous flux, scans the eye to be inspected 18. Similarly a value is determined to be $D_3$, which is obtained as a spherical refracting power from the phase difference of the electric signals from ON to OFF, which is outputted from the couple of photoelectric conversion elements 46a and 46b in the beam receiving part 38, in case that the rear edge in the moving direction of the luminous flux, scans the eye to be inspected 18, and a value is determined to be $D_4$, which is obtained as a spherical refracting power from the phase difference of the electric signals from ON to OFF, which is outputted from the other couple of the photoelectric elements 46c and 46d in case that the rear edge in the moving direction of the luminous flux scans the eye to be inspected 18. If the values of $D_1$, $D_2$, $D_3$, and $D_4$ are taken as above, as shown in the above Japanese Unexamined Patent Publication 165735/1982 etc., the following equations are established among $D_1$, $D_2$, $D_3$, and $D_4$, the spherical refracting power (S), the cylindrical axis angle ($\theta$) and cylindrical refracting power (C) of the eye to be inspected 18.

$$D_1 = S + C \cos^2\theta \quad (1)$$

$$D_2 = C/2 \sin2\theta \quad (2)$$

$$D_3 = -C/2 \sin2\theta \quad (3)$$

$$D_4 = S + C \sin^2\theta \quad (4)$$

Accordingly, by processing these simultaneous equations in the processing system, the spherical refracting power (S), the cylindrical refracting power (C) and the cylindrical axis angle ($\theta$) of the eye to be inspected can be obtained, respectively.

As explained in details as above, in the eye refractive power measuring device composed as above, the beam blocking plate for obtaining the luminous flux, is constituted as a plate-like body. Therefore, this beam blocking plate, compared with a circular shape body, is extremely easy to make or to work. Furthermore, the miniaturization and the light weight thereof, are favorably attained. The problem of the center oscillation or the like in the rotation of the plate, can be avoided as much as possible.

In this eye refracting power measuring device, the luminous flux projected to the eye to be inspected 18, can be formed in different shapes in which inclination angles at the front and rear edge parts in the moving direction, are different each other. The refractive power is calculated based on the electric signals from OFF to ON, and from ON to OFF, which are outputted by the photoelectric conversion elements 46a through 46d of the beam receiving part 38, in the case where front and rear edges of the luminous flux scan on the eye to be inspected 18. Therefore, it is not necessary to provide two different kinds of luminous fluxes having inclination angles different each other, as in the conventional slit-like luminous fluxes, and the measurement of the refracting power of an eye is performed by only one kind of luminous flux.

Accordingly, it becomes possible to unify the shape of the beam transmitting part which is formed on the plate 20, to obtain a luminous flux of a predetermined shape, and the forming thereof becomes easy.

Figure 6:
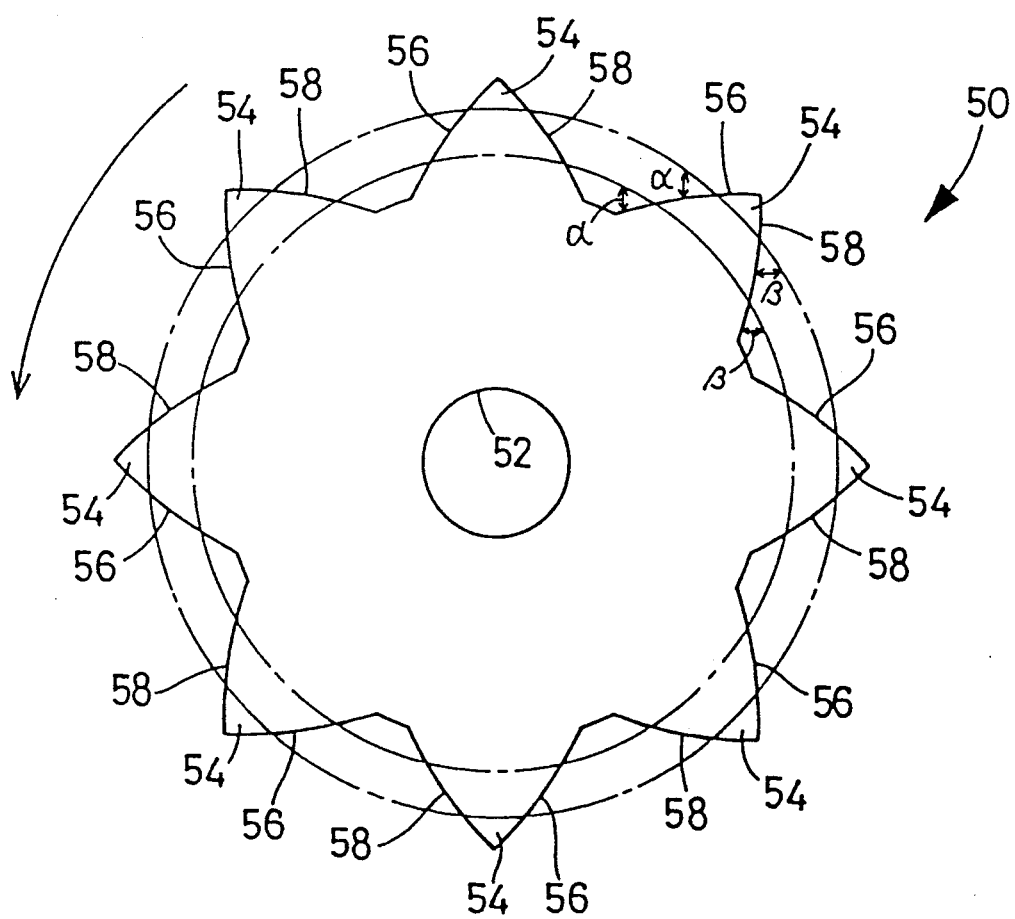
FIGS. 6, 7, 8, and 9 are front views showing the other embodiments of plates favorably utilized in the present invention.

Next, another embodiment is shown, in FIG. 6, of a plate favorably utilized in the eye refracting power measuring device according to the present invention.

In the plate 50 in this embodiment, as in the plate 20 in the first embodiment, the installing hole 52 is provided for the rotating shaft of the motor, at its center. The plate 50 is provided with a plurality (8 in this embodiment) of teeth 54 of the conversing shape, protruded outwardly in the radius direction from the center, which make the outer periphery of the plate 50 into a sawtooth shape.

In this plate 50, the front side 56 and the rear side 58 of the respective teeth 54, are formed in curves which intersect with the tangent lines of any concentric circle centered at the rotation center of the plate 50 by approximately constant inclination angles: $\alpha$ and $\beta$, at the intersection with the concentric circles, over the range of almost their total length. Furthermore, especially, in this embodiment, the intersection angles of the front side 56 and the rear side 58 with the tangential lines in circumferential direction, at the intersection with any circle centered at the rotation center of the plate 50, have a relative angle difference of 90° For instance, $\alpha$ and $\beta$ are set as $\alpha = 45°$ and $\alpha = 45°$.

Accordingly, by using the plate 50, even when the distance between the rotating shaft 22 of the plate 50 and the projecting beam 12 is changed and a circle as a locus of the center of the beam projecting path 12 on the plate 50, is deviated in the radius direction, the change of the inclination angles of the front and the rear edges of the luminous flux projected to the eye to be inspected 18, can be prevented quite effectively. The generation of the measurement error due to the deviation can be prevented as much as possible.

Figure 7:
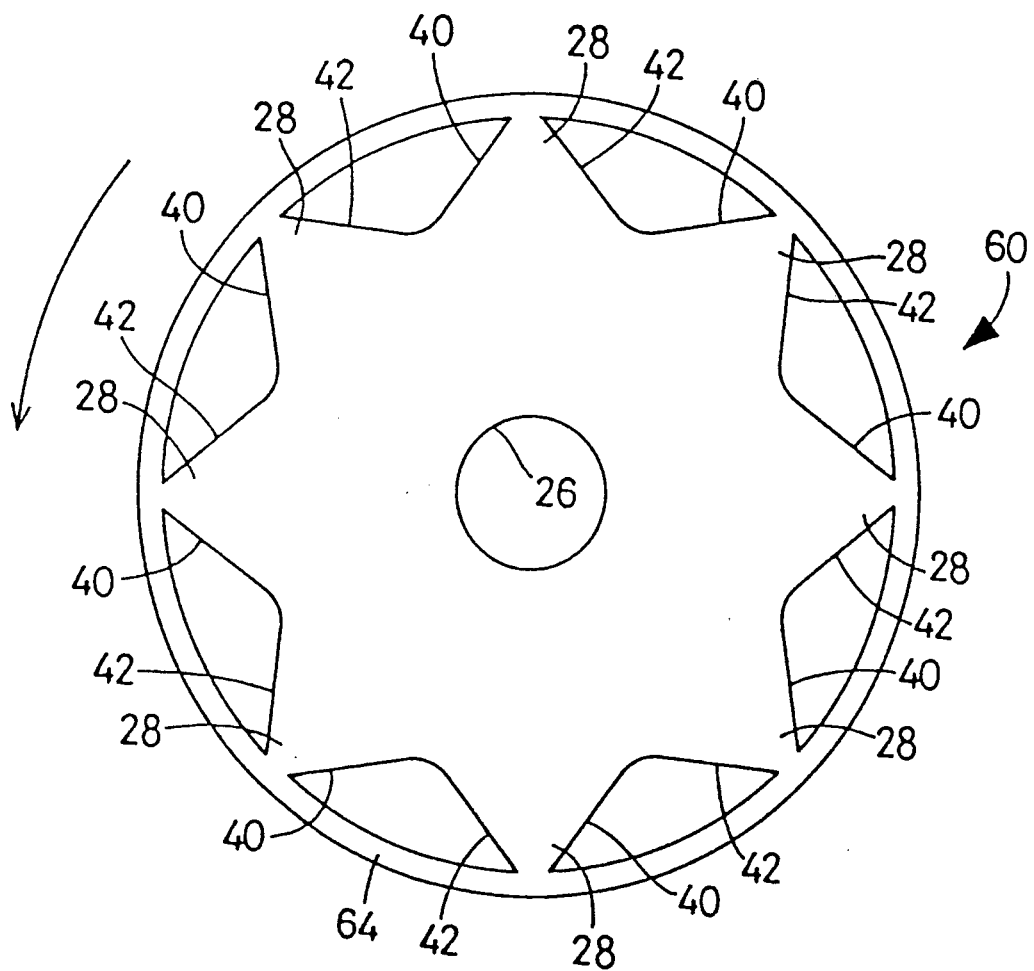
Figure 8:
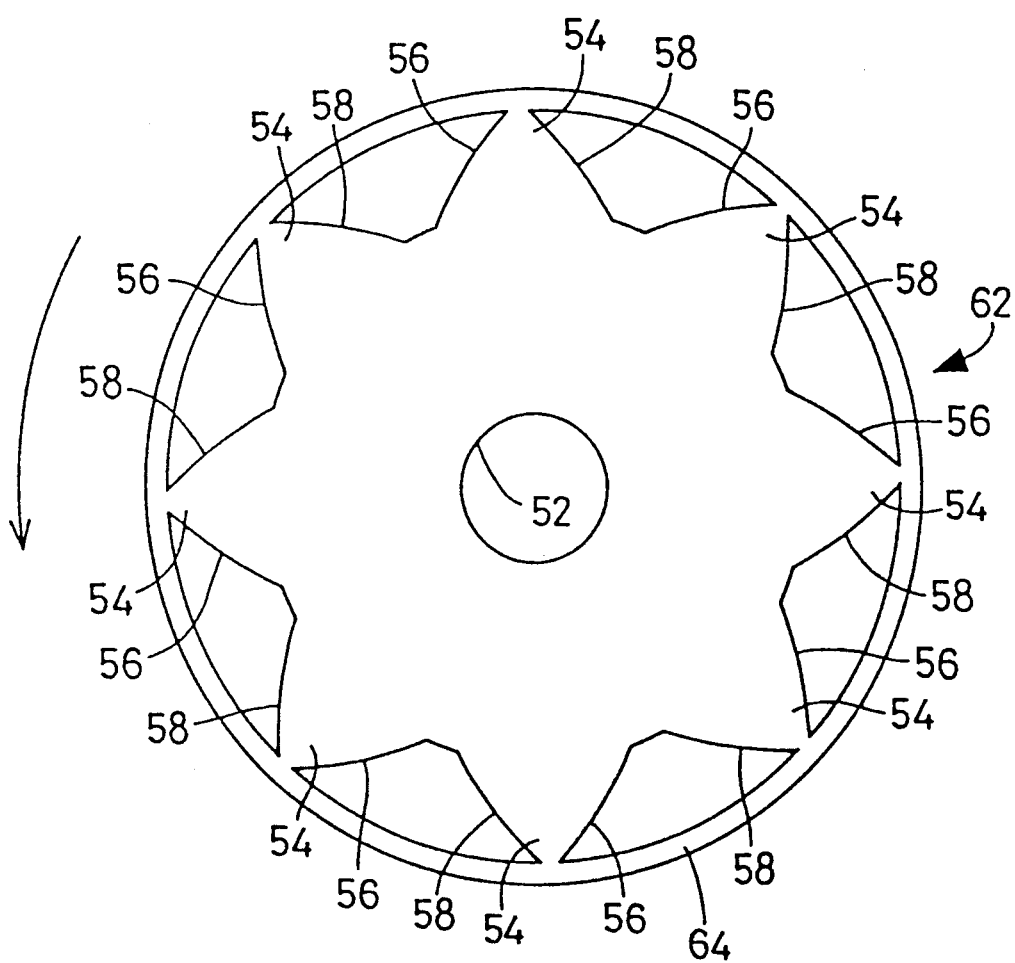

Furthermore, in FIGS. 7 and 8, embodiments of the plate favorably utilized in the eye refracting power measuring device according to the present invention are shown respectively, in which more improvement is made on the plate 20 and the plate 50 which are shown in the first and the second embodiments. Furthermore, in FIGS. 7 and 8, to facilitate the understanding, the same notations are designated to the parts similar to those in the first and the second embodiments.

In the plates 60 and 62 which are shown in FIGS. 7 and 8, the protective ring 64 of an annular shape is provided at the outer periphery, which are integrally connected to the tops of the teeth 28 and 54 respectively.

Accordingly, in the plates 60 and 62 of these embodiments, having the protective ring 64 integrally, even when fingers or hands touch the plates by accident in the high speed rotation (normally, 1,700 to 2,000 rpm), the safety is favorably provided.

Furthermore, by providing such protective ring 64, the strength of the plates 60 and 62, and especially those of the teeth 28 and 54 are enhanced, and an effect in which a deformation in the production and setting of the plate, is more favorably prevented, can be exhibited.

Figure 9:
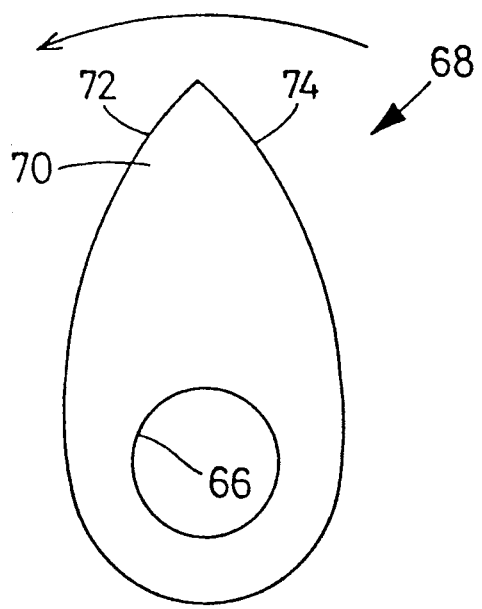

FIG. 9 shows another embodiment of the plate favorably utilized in the eye refractive power measuring device according to the invention.

In the plate 68 according to this embodiment, the installing hole 66 is provided for the rotating shaft of the motor at its center and the tooth 70 of the conversing shape which is protruded outward in the radius direction from the center, is provided at the outer periphery.

The front side 72 and the rear side 74 of the tooth 70 of the plate 68, is formed in curves, which intersect with any concentric circle centered at the rotation center of the plate 68 with approximately constant inclination angles, over a predetermined length of these edge parts. Furthermore, particularly, in this embodiment, similar to the above second embodiment, the intersection angles of the front side 72 and the rear side 74 with any concentric circle centered at the rotation center of the plate 68, are set as having a relative angle difference of 90°.

Accordingly, even in the plate 68 having only one tooth 70, by rotating it in the projecting beam path 12, and by intermittently blocking the beam path, as in the first embodiment, luminous fluxes are respectively obtained, in which the both edges in the moving direction, are respectively, inclined by respectively predetermined angles, and which can scan the eye to be detected 18.

Explanation is given in details to the embodiments of the present invention as above. These are only literal examples. Therefore this invention should not be interpreted by limiting the invention only to these examples.

For instance, the inclination angles of the front side and the rear side of the tooth formed on the plate, and the inclination angle difference, are never to be limited to the above embodiments. These can be modified according to the allocation of the photoelectric conversion elements in the beam receiving part, and to the methods of calculation in the treatment system in which the refracting power is calculated based on the output of the photoelectric conversion elements etc.

Furthermore, in case of the eye refracting power measuring device on the above embodiments, only the important parts of the construction are exemplified. Therefore the fixation observation target optical system, as shown in Japanese Unexamined Patent Publication No. 160538/1980, in which, for instance, a collimation axis of the eye to be inspected is fixed, to enhance the measurement accuracy further, can favorably added.

Furthermore, it is possible to obtain the refracting power, by adding a so called automatic fogging device, disclosed in Japanese Unexamined Patent Publication No. 165735/1982, and by repeating the movement of the observation target until the refracting power of the eye to be inspected does not change, based on the refracting power calculated by a processing system of the device per se.

Furthermore, in the processing system in the eye refracting power measuring device according to the above embodiments, the refracting power is obtained by the calculation based on the phase difference of the output signals from the beam receiving parts. However, as disclosed in Japanese Unexamined Patent Publication No. 165735/1982, it is possible to perform the measurement utilizing a model eye, after the completion of the device, and to memorize the output values of the respective photoelectric conversion elements on that occasion, (phase differences) in the treatment system, corresponding to a known refracting power of the model eye. By doing that, the allocation of the parts which constitute the beam projecting optical system and the beam condensing optical system, is comparatively flexibly carried out. Furthermore, in case that the outputs of the respective photoelectric conversion elements and the refracting power of the eye to be inspected, are correlated and the correlation is inputted to the processing system, it is not necessary to correlate the inclinations of the front and the rear edges of the luminous flux projected on the eye to be inspected, with the allocation mode of the photoelectric conversion elements of the beam receiving part 38 which receives the reflection beam.

Furthermore, in the above embodiment, the plate is disposed between the beam source 10 and projecting lens 14. However the plate may be disposed between the projecting lens 14 and the half mirror 16 or the like.

In the above embodiments, the number of teeth formed on the plate are one and eight. However the number should not be limited.

In the above embodiments, an example is shown in which this invention is applied to the eye refracting power measuring device. However this invention can be applied to, for instance, a lens meter or a measuring device of a corneal radius of curvature without any modification in principle.

Although not enumerated, this invention, based on the knowledge of the artisan, can be applicable to embodiments in which various alterations, modifications, and improvements are added. These embodiments are in the scope of this invention, as far as the gist of the invention is not deviated.

As apparent in the above explanation, according to the refracting power measuring device of an optical system of the present invention, the beam projecting path is intermittently blocked, and the light blocking body which forms the luminous flux projected to the optical system to be inspected, is composed of a rotating plate of a planar shape. Therefore compared with the conventional cylindrical shape, the production and the working thereof are extremely easy, in which the miniaturization and the light weight thereof are easily attained favorably, and the problem such as the center oscillation in the rotation is effectively evaded.

Furthermore in the refracting power measuring device according to the present invention, when the front and the rear edges of a luminous flux scan an optical system to be detected, the refractive power is obtained based on the phase difference of electric signals of OFF to ON and ON to OFF, which are outputted by the photoelectric conversion elements of the condensing optical system. Therefore it is not necessary to utilize two kinds of luminous fluxes of which inclination angles are different each other as in the conventional slit-like luminous fluxes. It is possible to carry out the measurement by only one kind of luminous flux. Therefore in order to obtain such luminous flux, the shape of the beam transmitting part which is formed on the rotating plate, can be unified, which facilitates the forming thereof further.

In the refracting power measuring device having the feature in which both sides of the teeth of the rotating plate are formed by curves which intersect by about constant inclination angle with any concentric circle centered at the rotation center, even when the allocation distance between the beam projecting path of the luminous flux projected on a detected optical system to be inspected, and the rotating plate, is changed more or less, the change of the inclinations of the front and the back edges of the obtained luminous flux, is effectively prevented. Therefore the measurement error due to the change is prevented as far as possible.

Furthermore, in accordance with the feature of the refracting power measuring device in which a protective ring is integrally provided at the outer periphery of the rotating plate, in case that fingers or hands touch the device by accident in the rotational operation, the safety is favorably provided.

We claim:

1. An apparatus for measuring a refracting power of an optical system which comprises:
   a beam projecting optical system which projects a predetermined moving luminous flux to an optical system to be inspected;
   a beam condensing optical system in which a photoelectric conversion element receives a luminous flux transmitted through the optical system to be inspected; and
   a processing system which obtains the refracting power of the optical system to be inspected, based on an output from the beam condensing optical system;
   wherein a rotating plate having at least one tooth of a converging shape, which is protruded outwardly from a center of the rotating plate, is disposed in a beam path of the beam projecting system such that said at least one tooth passes through the beam path as said rotating plate rotates; and
   wherein said at lest one tooth includes two sides which are inclined at different angles from one another with respect to a moving direction of the tooth such that a luminous flux is produced as said rotating plate rotates to pass said tooth through the beam path with the tooth thereby intermittently blocking the beam path, said luminous flux irradiating the optical system to be inspected.

2. The apparatus for measuring a refracting power of an optical system according to claim 1, wherein the both sides of the tooth of the rotating plate is formed in curves, which intersect with a circle being concentric with respect to a rotation center of the rotating plate by substantially constant intersecting angles, in a predetermined range of a radius of the circle.

3. The apparatus for measuring a refractive power of an optical system according to claim 1, or claim 2 further comprising; a protective ring, being disposed at an outer periphery of the rotating plate, which is connected to a top end of the tooth, and is integrally installed with the rotating plate.

* * * * *